US005582190A

United States Patent [19]
Slavin et al.

[11] Patent Number: 5,582,190
[45] Date of Patent: Dec. 10, 1996

[54] ARTHROSCOPIC SURGICAL DEVICE AND METHOD FOR EVALUATING AND RELIEVING THE SYMPTOMS OF TEMPOROMANDIBULAR JOINT DISORDERS

[75] Inventors: Andrew B. Slavin, 349 Eagle Dr., Jupiter, Fla. 33477; Timothy J. Shea, Oviedo; David G. Cheeseman, Orlando, both of Fla.

[73] Assignee: Andrew B. Slavin, Jupiter, Fla.

[21] Appl. No.: 328,735

[22] Filed: Oct. 25, 1994

[51] Int. Cl.$^6$ .................................................. A61B 17/36
[52] U.S. Cl. .............................. 128/898; 606/15; 606/13; 606/1; 600/108
[58] Field of Search .................................. 606/7, 13–15, 606/1; 600/108, 130, 156; 128/898

[56] References Cited

U.S. PATENT DOCUMENTS

| | | |
|---|---|---|
| 4,072,147 | 2/1978 | Hett . |
| 4,141,362 | 2/1979 | Wurster . |
| 4,211,229 | 7/1980 | Wurster . |
| 4,313,431 | 2/1982 | Frank ........................................ 600/108 |
| 4,848,336 | 7/1989 | Fox et al. ..................................... 606/7 |
| 4,959,063 | 9/1990 | Kojima ........................................ 606/15 |
| 5,123,902 | 6/1992 | Muller et al. . |
| 5,178,616 | 1/1993 | Uemiya et al. . |
| 5,195,541 | 3/1993 | Obenchain ................................. 606/15 |
| 5,201,729 | 4/1993 | Hertzmann ................................. 606/15 |
| 5,217,454 | 6/1993 | Khoury ........................................ 606/7 |
| 5,423,804 | 6/1995 | Kulick ......................................... 606/15 |

*Primary Examiner*—Angela D. Sykes
*Assistant Examiner*—Michael Peffley
*Attorney, Agent, or Firm*—Allen, Dyer, Doppelt, Franjola & Milbrath, P.A.

[57] ABSTRACT

A device and method are provided for evaluating and relieving the symptoms associated with joint disorders. The cannula device has two channels extending from the proximal end to the distal end. The first is used to retain an arthroscope; the second, an optical fiber for transmitting laser radiation. In a particular embodiment, the device may be used for performing surgical procedures within a temporomandibular joint space including, but not limited to, releases, myotomies, and coagulation. This arrangement permits the collocation of the visualizing and surgical implements, obviating the need for triangulation by the surgeon. A third channel is provided for the introduction of irrigating fluid into the joint space. The method disclosed includes inserting the cannula into the joint space, inserting the arthroscope and fiber into their respective channels, and positioning them to perform the desired procedure.

9 Claims, 4 Drawing Sheets

ARTHROSCOPIC SURGICAL DEVICE AND METHOD FOR EVALUATING AND RELIEVING THE SYMPTOMS OF TEMPOROMANDIBULAR JOINT DISORDERS

BACKGROUND OF THE INVENTION

1. Field of the Invention

The present invention relates to surgical procedures, and, more particularly, to methods of performing surgery to alleviate the discomfort caused by temporomandibular joint syndrome.

2. Description of Related Art

Temporomandibular joint (TMJ) syndrome (or dysfunction) is a disorder of the joint between the lower jaw and the skull. The temporomandibular joint lies between the temporal bone of the skull and the mandible of the jaw, and allows the jaw to open and close. The joint is formed by a condyle, or protuberance, on the mandible, which hinges and glides in and out of the fossa, or depression, in the temporal bone (see FIG. 1).

TMJ syndrome can be caused by grinding of the teeth, malocclusion, trauma, and arthritis. There is also an indication that a posterior or backward displacement of the condyle of the jaw significantly contributes to TMJ pain [L. A. Weinberg and J. K. Chastain, *J. Am. Dental Assoc.* 120(3), 305 (1990)]. The effects can range from mild to severe, including pain in the joint area o that can extend to the shoulders, back, neck, and sinuses. TMJ-related headaches can also ensue, with pain sufficiently severe so as to cause nausea and blurred vision. Treatment can likewise range in extent, and may include exercise, the use of drugs or bite guards, massage, biofeedback, or electrical stimulation. Surgery is utilized in the most severe cases, which represent approximately 10% of those seeking treatment.

At present, arthroscopic techniques are prevalent in TMJ surgery. Typically, two small incisions are made in front of the ear, and a fiber-optic device is inserted into the joint. The fiber transmits an image of the joint to a screen, on which the surgeon can view the procedure indirectly without having to create the relatively large incision that would be necessary for direct visualization. Surgical implements are passed through the second incision.

Single-puncture techniques have also been taught for diagnostic arthroscopy. In these methods, a line is drawn from the mid-tragus of the ear to the lateral canthus of the eye. While the mandible is held in a protracted position, a needle is inserted into the superior joint space. The joint space is insufflated with local anesthesia with vasoconstrictors.

The maximum concavity of the glenoid fossa, which is the target for the puncture, is palpated and marked. The mandible is kept in a fully protracted position to open the posterior joint space.

A trocar is inserted into a cannula and is used to create the puncture wound, aiming at the ledge of the zygomatic arch. When the ledge is palpated by the trocar, the trocar is moved through the joint capsule with a swivelling motion. Resistance is felt until the tip of the trocar enters the joint space, at which point the trocar is removed and a blunt obturator is inserted for advancement of the cannula into the joint. The blunt obturator is used to prevent laceration of tissue, and typically advances to a depth in the range of 25 to 45 mm, after which it is removed.

The joint is then lavaged (irrigated) to remove blood, puncture debris, and synovial fluid by gradually introducing 20–25 cc of Ringer's saline solution. After flushing, an arthroscope is inserted.

Such previously used procedures require triangulation on the part of the surgeon, since the viewing means and surgical implements are inserted through nonparallel portals. In addition, the inferior joint space is normally too small for access by two rigid instruments, and thus procedures in this area must be performed "blind."

SUMMARY OF THE INVENTION

It is thus an object of the present invention to provide an improved arthroscopic method for performing a surgical procedure within a joint space of a patient without the need of triangulation between the viewing means and the surgical cutting means within the joint space.

It is a further object to provide an arthroscopic method for lower temporomandibular joint space evaluation and surgical procedures with the use of a single-portal technique.

It is an additional object to provide a cannula device for use in an arthroscopic procedure on a joint, the cannula device permitting collocation of viewing means and surgical cutting means.

It is yet another object to provide a cannula device having two channels therethrough, one of the channels carrying an optical fiber for the transmission of laser radiation for performing surgical procedures.

It is yet a further object to provide the aforesaid cannula device having an optical fiber sheathed in a semirigid material to protect the distal tip of the fiber during a surgical procedure.

These and other objects are provided with the device and method of the present invention. The device of the invention comprises a cannula having a proximal end and a distal end. A first and a second channel each extend from the proximal end to the distal end and are generally parallel at the distal end. The first channel is dimensioned to permit visualizing means to pass therethrough, the visualizing means typically taking the form of an arthroscope. The second channel is dimensioned to permit optical fiber means to pass therethrough. The optical fiber means typically take the form of a fiber for transmitting laser radiation into the surgical site.

The cannula having two channels passing therethrough permits collocation of the visualizing means and the distal tip of the optical fiber means within a unitary cannula during a surgical procedure, thus permitting direct visualization of the site without triangulation.

In one embodiment, a third channel is provided in the cannula, also extending from the proximal to the distal end. This channel has a port at the proximal end and is used for the introduction of irrigating fluid into the joint space.

In a further embodiment, the optical fiber is sheathed in a semirigid material to protect the distal tip of the fiber against breakage during the surgical procedure.

The arthroscopic method is provided by the present invention for performing a surgical procedure within a joint space and for relieving symptoms caused by joint disorder. The method comprises the steps of providing a dual-channel cannula as described above and inserting the cannula into the joint space.

Next visualizing means are inserted into the first channel of the cannula, the visualizing means typically comprising an arthroscope. These visualizing means are then positioned to permit visualization of a desired area of the joint space.

Optical fiber means having a distal end are then inserted into the second channel of the cannula. The optical fiber means, typically a silica fiber, is in optical communication with laser means and is designed to transmit the radiation emitted by the laser means.

The distal end of the optical fiber means are positioned to perform a desired surgical procedure, the positioning being accomplished with the aid of the visualizing means. Finally the desired surgical procedure is performed with the use of radiation transmitted from the laser means through the optical fiber means and further with the aid of the visualizing means.

The cannula of the present invention can in particular be utilized in evaluating and treating disorders within both the upper and the lower temporomandibular joint spaces of a patient. The steps of the method are as above. In the specific case of the lower temporomandibular joint, the cannula is inserted into the lower joint space of the patient, which is usually not accessible by previously used instrumentation.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

Figure 1:
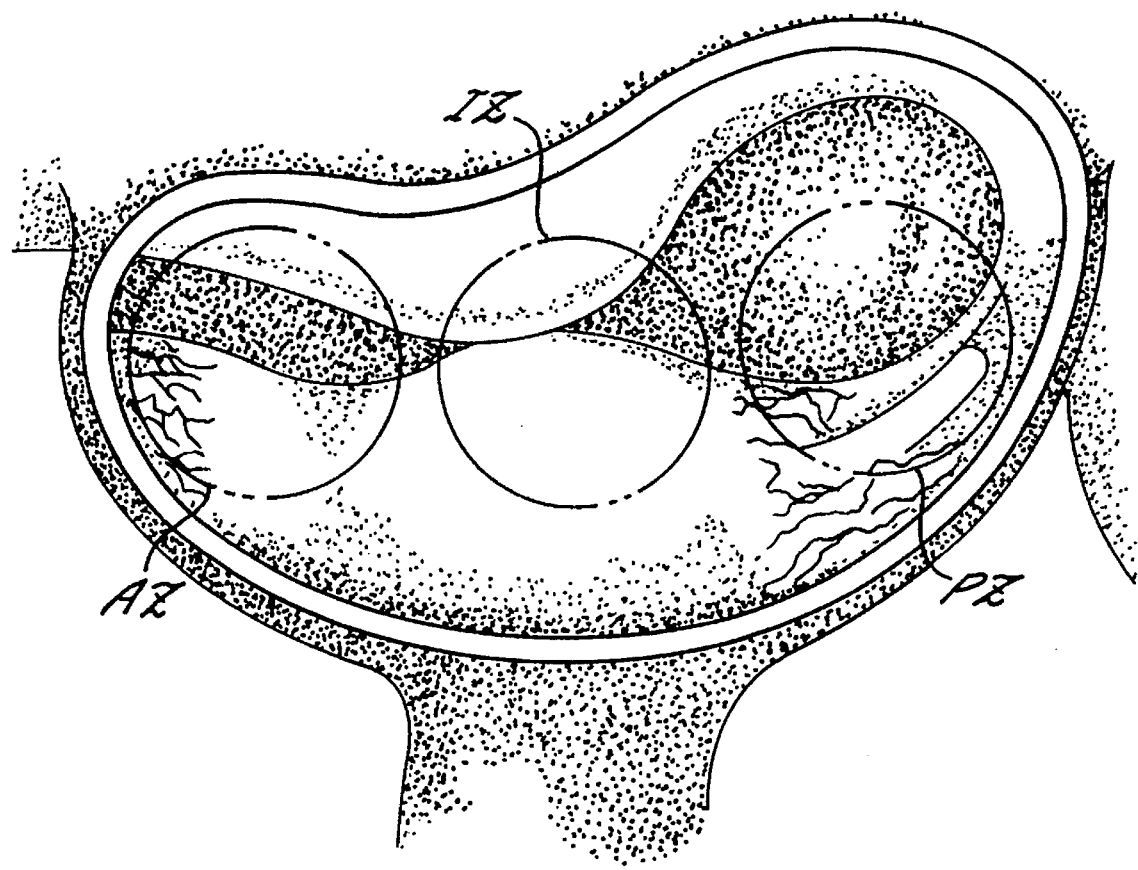
FIG. 1 illustrates the anatomy of the temporomandibular joint.
Figure 2:
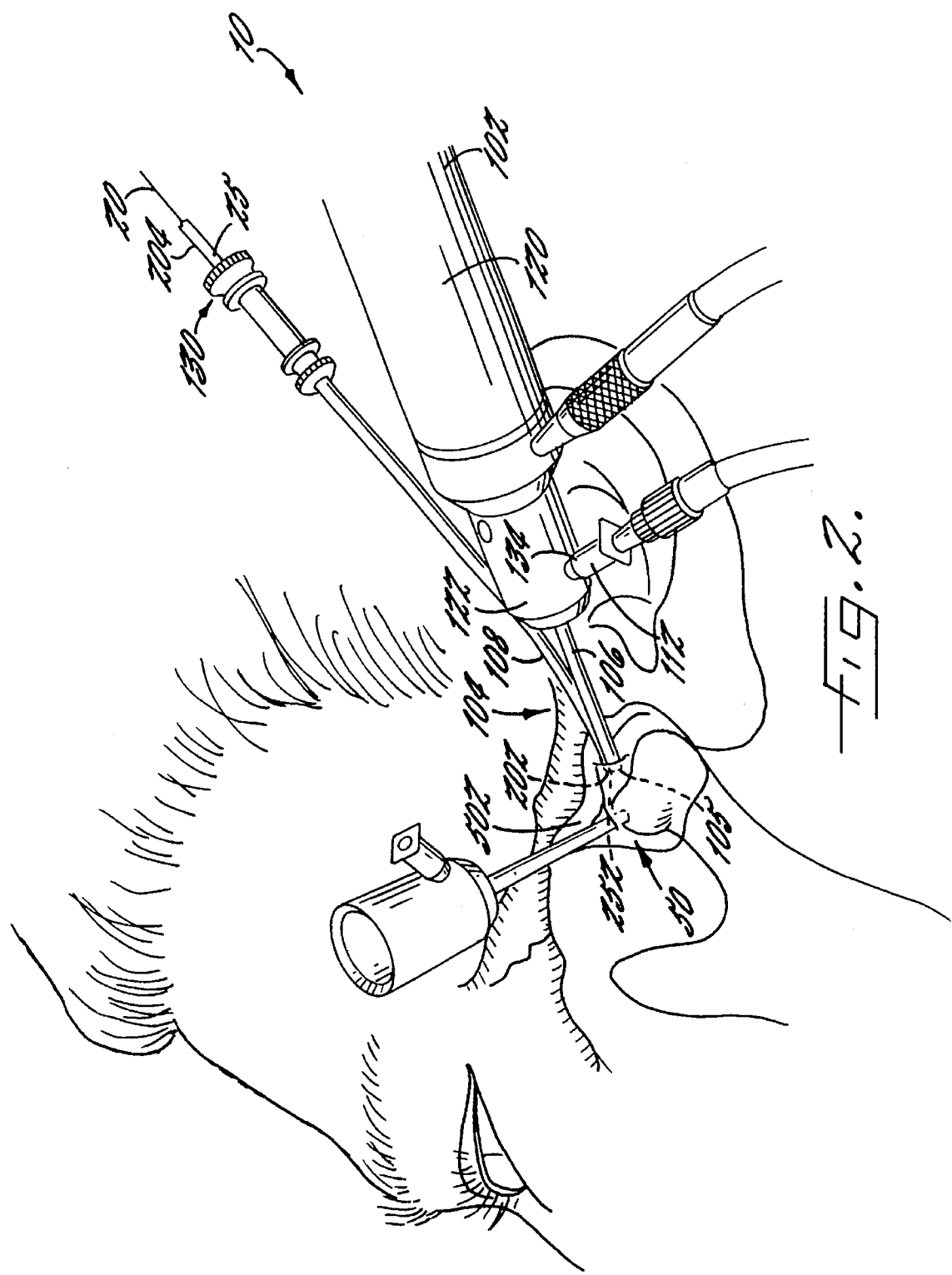
FIG. 2 illustrates a surgical method for evaluating and treating disorders of the temporomandibular joint.
Figure 3:
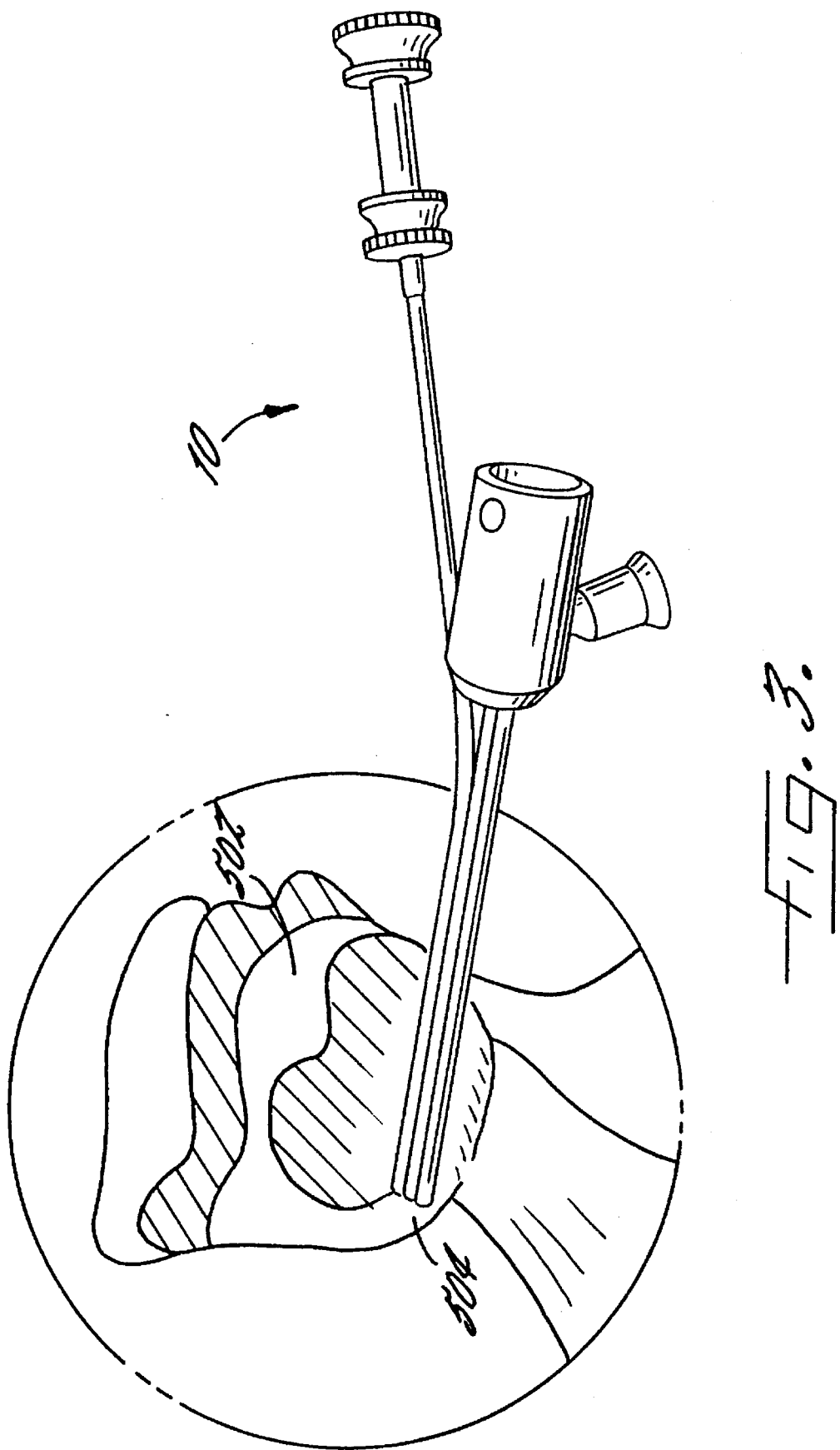
FIG. 3 illustrates a surgical method for evaluating and treating disoders of the lower joint space.
Figure 4:
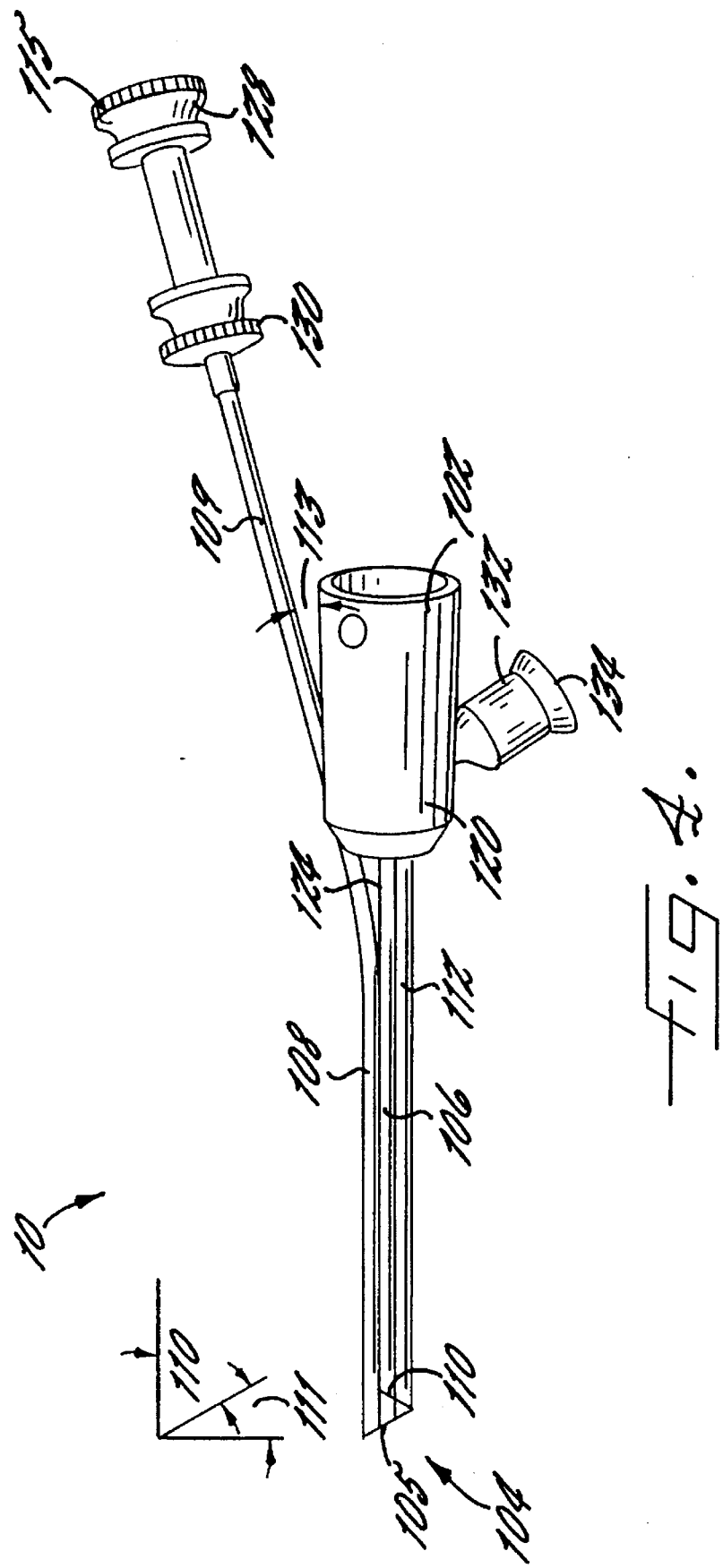
FIG. 4 is a side view of a preferred embodiment of the dual-channel cannula of the present invention.

A description of the preferred embodiments of the device and method of the present invention will now be presented with reference to FIGS. 2–4.

The Dual-Channel Cannula

The preferred embodiment of the cannula device 10 of the present invention is illustrated in FIG. 4. Cannula 10 has a proximal end 102 and a distal end 104. Proximal end 102 is widened and remains outside the patient during a surgical procedure. Distal end 104 is generally cylindrical in shape and has a tip 105 that slants at an interior angle 110 of approximately 60 degrees. [This slanting end provides that tip 105 is pointed.] The diameter of distal end 104 is approximately 2.7 mm.

In the preferred embodiment cannula 10 has a first 106, a second 108, and a third 112 channel extending from the proximal 102 to the distal 104 end.

The first channel 106 is generally cylindrical, having a widened, also generally cylindrical portion 120 of diameter 2.4 mm at the proximal end 102 and a narrowed portion 122 of diameter approximately 2 mm extending to the distal end 104. First channel 106 is dimensioned to permit visualizing means in the form of a 1.9-mm, 30 degree arthroscope to pass therethrough. The slant angle 110, having a complementary angle 111 of 30 degrees, thus provides a field of view of 30 degrees at the distal end 104.

The second channel 108 has a proximal portion 109 that extends at an acute angle 113 from side wall 124 of channel 106 and proceeds to distal end 104 in generally parallel fashion to first channel 106. Second channel 108 is dimensioned to permit optical fiber means to pass therethrough (see FIG. 2), the optical fiber means having transmissive properties in a desired wavelength range. In the preferred embodiment the optical fiber means comprises a 200-micrometer silica fiber 20 having a distal tip 202 and a proximal end 204. In a further embodiment fiber 20 is surrounded by a stainless steel sheath 25 that serves to protect the distal tip 202 of fiber 20 against breakage when it is being inserted into the second channel 108 of cannula 10 and positioned during the surgical procedure. Sheath 25 and fiber 20 are dimensioned to be passed through cannula means in general, and, specifically, through second channel 108. [Sheath 25 has a pointed distal tip 252 that will be seen in the following to serve as a suture needle.]

In the embodiment shown in FIG. 4, the proximal portion 109 of second channel 108 further comprises a thumbwheel 130 and a flared end 128 at the proximal end 115. Flared end 128 facilitates the insertion of fiber 20 into second channel 108. Thumbwheel 130 permits advancement and retraction of fiber 20 within second channel 108.

Third channel 112 enters the proximal end 102 via a port 134 in cylindrical protrusion 132. Port 134 is positioned generally diametrically opposite protrusion 126, also emerging from sidewall 124 of first channel 124. Third channel 112 is used to introduce irrigating fluid into the surgical site.

The Temporomandibular Joint Surgical Method

The preferred embodiment of the method of the present invention provides protocols for performing surgical procedures within a temporomandibular joint space 50, for relieving symptoms caused by temporomandibular joint disorder, and for evaluating such disorders comprises the steps as detailed in the following. Other embodiments may be contemplated within other joint spaces.

After the patient is anesthetized and prepared for surgery, a line is drawn from the posterior aspect of the tragus of the ear to the lateral canthus of the orbit. Two marks are then made, one 10 mm anterior to the posterior aspect of the tragus of the ear, and a second 10 mm anterior to the first mark and 9 mm below the line.

Next a solution of lidocaine and epinephrine is injected into the superior joint space 502, thereby providing distention thereof. Specifically, the solution comprises 1 cc of 2% Xylocaine™ 1:100000 epinephrine solution.

Using a #11 blade, a first and a second vertical incision are made at the site of the two marks, each 3 mm in length.

A first and a second 2.0 mm cannula and a first and a second blunt trocar are used to dissect down to the lateral capsule overlying the superior joint space and perforate the superior joint space 502 bluntly. The first and the second cannula are advanced, and the first and the second trocar are removed.

An irrigation system 60 is established to wash out the joint space, after which an arthroscope is placed through the first cannula into the joint, allowing direct visualization of all joint structures. A switching stick is then placed through the second cannula, and the second cannula is removed. These steps, not illustrated, are well known in the art.

The dual-channel cannula 10 described above is inserted over the switching stick into the anterior recess of the superior compartment 502 of the joint, and the switching stick is removed. As shown in FIG. 2, the irrigation system is reconnected through the third channel 112 of the dual-channel cannula 10, the arthroscope is locked into the first channel 106, and an optical fiber 20 is inserted into the second channel 108. The optical fiber 20 in general is utilized as a radiation transmitting means between an internal surgical site and an external site. Specifically, in the preferred embodiment a 200-micrometer silica fiber is used for channeling radiation from a holmium laser emitting at 2.1 micrometers. Also in the preferred embodiment the fiber is encased in a stainless steel sheath 25 to protect the fiber against breakage during insertion and manipulation.

Utilizing the arthroscope for direct visualization, the distal tip 202 of the optical fiber 20 is positioned at the desired location. This positioning may be assisted in an embodiment wherein the second cannula 62 is not removed from the joint space 50 but is used as a conduit through which is passed a surgical manipulator, as is well known in the art. This manipulator may then be used to position the distal end 202 of the optical fiber 20. Then with the use of the radiation emitted by the laser, a desired surgical procedure is performed within the joint space under direct visualization via the arthroscope.

One surgical procedure that can be performed comprises an anterior release from the medial to the lateral capsule down to the lateral pterygoid muscle. In previously disclosed techniques, the anterior lateral portion, which may comprise up to half of the release, cannot be visualized. Coagulation may also be achieved with the radiation emitted from the fiber. In addition, a lateral pterygoid myotomy may be completed with the laser radiation. Other procedures that may be performed include synovectomy, laser debridement of adhesions and cartilage, partial meniscectomy, bone spur removal, and posterior attachment tissue welding for treating hypermobility syndrome. In general, all tissue that can be visualized can be lased, since the fiber is delivered to the same location as the viewing area. Therefore, tissues inaccessible under previous techniques owing to the limits of triangulation are easily accessible using the dual-channel cannula.

The dual-channel cannula 10 of the present invention can be used to perform lower joint space 504 evaluation and operative procedures, which are impossible with multiple portal techniques because of the reduced size of this compartment. In this procedure, illustrated in FIGS. 3, a small puncture is made through the lateral capsule into the inferior compartment and the dual-channel cannula is placed with the use of a switching stick. The surgery is performed as above with the aid of the arthroscope for visualization and the optical fiber for transmitting laser radiation.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction. In particular, other surgical techniques may be envisioned as employing the dual-channel cannula disclosed herein, such as other intracavity arthroscopic procedures.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. An arthroscopic method for relieving symptoms caused by temporomandibular joint disorder in a patient, the method comprising the steps of:

injecting a solution of lidocaine and epinephrine into a superior joint space of a temporomandibular joint of a patient, thereby providing distention thereof;

making a first vertical incision anterior to the posterior aspect of the tragus of the ear of the patient;

making a second vertical incision anterior to the first incision and below a line from the posterior aspect of the tragus of the ear to the lateral canthus of the orbit;

perforating the superior joint space bluntly with a first cannula and a first blunt trocar inserted into the first vertical incision and a second cannula and a second blunt trocar inserted into the second vertical incision;

advancing the first and the second cannula;

removing the first and the second trocar;

placing an arthroscope through the first vertical incision, allowing direct visualization of the joint;

placing a switching stick through the second vertical incision;

removing the second cannula;

providing a dual-channel cannula having a distal end, a proximal end, a first and a second channel, each extending from the proximal to the distal end;

inserting the dual-channel cannula over the switching stick into an anterior recess of the superior compartment of the joint;

removing the switching stick;

locking the arthroscope into the first channel of the dual-channel cannula;

inserting an optical fiber into the second channel of the dual-channel cannula, the optical fiber for channeling radiation from a holmium laser; and performing a desired surgical procedure within the joint space.

2. An arthroscopic method for relieving symptoms caused by temporomandibular joint disorder in a patient, the method comprising the steps of:

distending a superior joint space of a temporomandibular joint of a patient;

making a first vertical incision anterior to the posterior aspect of the tragus of the ear of the patient;

making a second vertical incision anterior to the first incision and below a line from the posterior aspect of the tragus of the ear to the lateral canthus of the orbit;

perforating the superior joint space with a first cannula and a first trocar inserted into the first vertical incision and a second cannula and a second trocar inserted into the second vertical incision;

advancing the first and the second cannula;

removing the first and the second trocar;

placing an arthroscope through the first vertical incision, allowing direct visualization of the joint;

placing a switching stick through the second vertical incision;

removing the second cannula;

providing a third cannula having a distal end, a proximal end, and a first and a second channel, each extending from the proximal to the distal end;

inserting the third cannula over the switching stick into an anterior recess of the superior compartment of the joint;

removing the switching stick;

locking the arthroscope into the first channel of the third cannula;

inserting an optical fiber into the second channel of the third cannula, the optical fiber for channeling laser radiation; and performing a desired surgical procedure within the joint space.

3. The method recited in claim 2, wherein the third cannula further has a third channel extending from the proximal end to the distal end, the proximal end having a port communicating with the third channel, and further comprising the step of irrigating the joint space throughout the procedure by introducing fluid through the port into the third channel of the third cannula.

4. The method recited in claim 2, wherein the optical fiber inserting step comprises inserting an optical fiber in optical communication with a holmium laser emitting 2.1-micrometer radiation.

5. The method recited in claim 4, wherein the optical fiber inserting step comprises inserting a 200-micrometer silica fiber.

6. The method recited in claim 5, wherein the optical fiber inserting steps further comprises inserting a sheath surrounding the silica fiber for protecting the distal tip of the fiber during the inserting and positioning steps.

7. The method recited in claim 6, wherein the optical fiber inserting step comprises inserting a sheath comprising stainless steel.

8. The method recited in claim 4, wherein the performing step comprises the steps of:

performing an anterior release from the medial to the lateral capsule down to the lateral pterygoid muscle of the patient with the use of the 2.1-micrometer radiation emitted from the distal tip of the fiber;

coagulating the surrounding vessels with the use of the 2.1-micrometer radiation emitted from the distal tip of the fiber; and performing a lateral pterygoid myotomy with the use of the 2.1-micrometer radiation emitted from the distal tip of the fiber.

9. The method recited in claim 2, wherein the performing step comprises the step of performing a surgical procedure selected from the group consisting of synovectomy, laser debridement of adhesions and cartilage, partial meniscectomy, bone spur removal, and posterior attachment tissue welding.

\* \* \* \* \*